United States Patent [19]

Gundelfinger

[11] Patent Number: 4,792,396
[45] Date of Patent: Dec. 20, 1988

[54] MULTI-SIZE INJECTOR PORT SYSTEM

[75] Inventor: Richard Gundelfinger, Cotati, Calif.

[73] Assignee: Rheodyne Incorporated, Cotati, Calif.

[21] Appl. No.: 116,387

[22] Filed: Nov. 3, 1987

[51] Int. Cl.⁴ .............................................. B01D 15/08
[52] U.S. Cl. .................................. 210/198.2; 55/386; 210/656
[58] Field of Search .......... 73/864.81, 864.83–864.87, 73/864.21, 863.71–863.73, 61.1 C; 422/103; 55/386, 67, 197; 210/198.2, 656

[56] References Cited

U.S. PATENT DOCUMENTS

| | | | |
|---|---|---|---|
| 4,026,803 | 5/1977 | Abrahams et al. | 55/386 |
| 4,083,702 | 4/1978 | Hartigan et al. | 55/386 |
| 4,182,184 | 1/1980 | Bakalyar et al. | 73/864.87 |
| 4,242,909 | 1/1981 | Gundelfinger | 73/864.21 |

FOREIGN PATENT DOCUMENTS 2847308  5/1979  Fed. Rep. of Germany ........ 55/386

Primary Examiner—Stewart J. Levy
Assistant Examiner—Robert R. Raevis
Attorney, Agent, or Firm—Freilich, Hornbaker, Rosen & Fernandez

[57] ABSTRACT

A frame is described, that is part of an injector which is used to load a sample at high pressure into a chromatographic column, wherein a tube coupling hole in the frame can not only couple to a standard 1/16th inch tube, but can also couple to a much smaller diameter tube which is useful for minimizing dispersion when small samples or small chromatographic columns are used. The tube coupling hole has a cylindrical inner end portion of a diameter substantially equal to the smaller tube diameter to closely receive it, a tapered middle portion, and a threaded outer portion. Ferrules for sealing tubes to the tapered hole portion, include a first ferrule having a hole that closely surrounds the smaller diameter tube, with the end of the tube lying in the cylindrical inner end portion. A second ferrule has a hole that closely surrounds the standard size larger tube, the tip of the larger tube lying against the tapered hole portion.

8 Claims, 2 Drawing Sheets

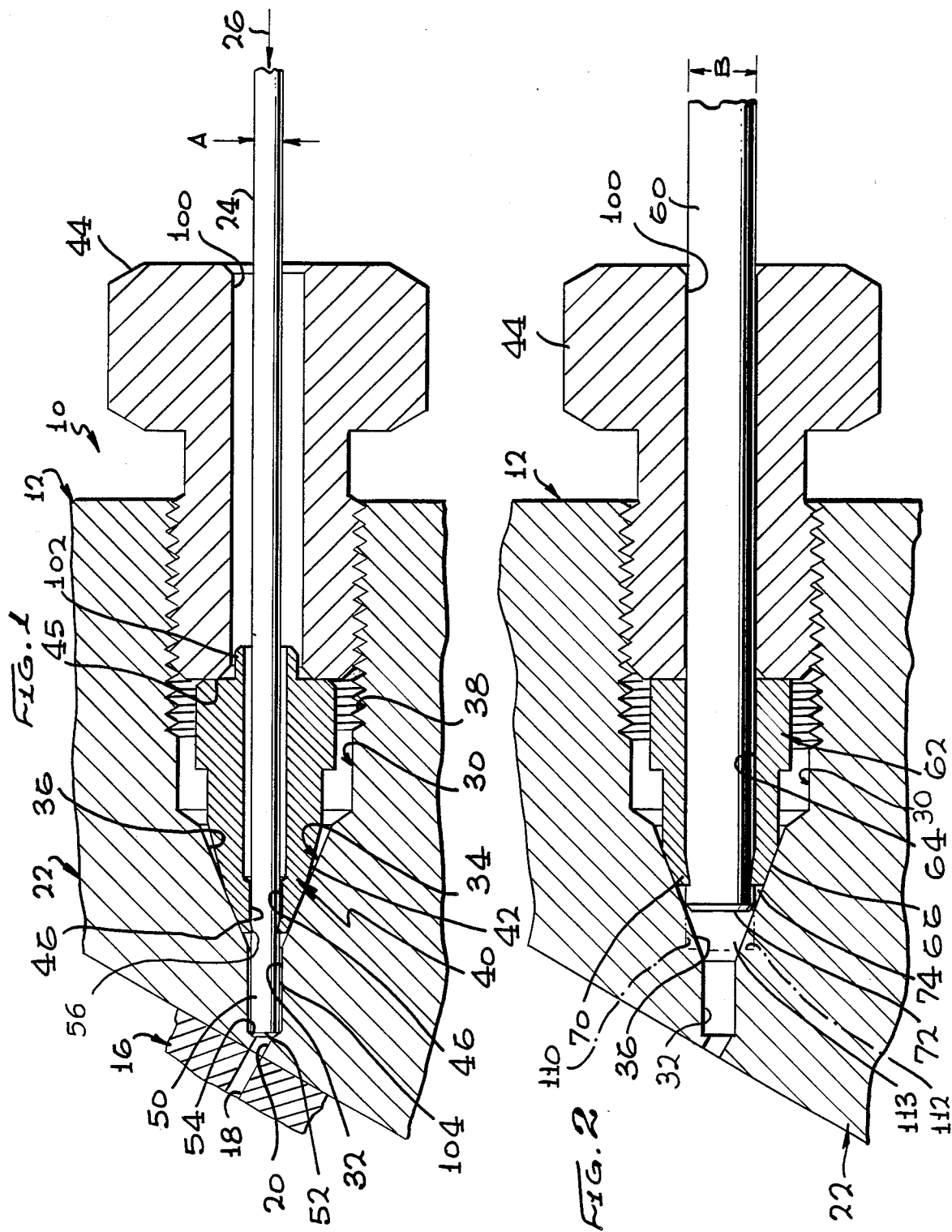

MULTI-SIZE INJECTOR PORT SYSTEM

BACKGROUND OF THE INVENTION

In liquid chromatography, which is used to analyze small fluid samples, it has become common practice to use a sample injection device which receives a liquid sample at substantially atmospheric pressure and stores it in a sample loop formed by a small diameter but long length tube. Upon subsequent actuation of the injector device, the sample is swept at a high pressure, typically 100 to 10,000 psi from the sample loop to a chromatographic column, by a solvent received from a high pressure pump. It is important to minimize mixing of the sample with solvent, since such mixing can cause the leading edge of the sample entering the chromatographic column to represent a mixture of the sample to be analyzed and the solvent, such mixing often being referred to as dispersion.

It is common practice to provide a tube coupling hole in the frame of the injector and column devices, which receive ends of the small diameter tube in an arrangement that minimizes dispersion. U.S. Pat. No. 4,182,184 shows such a tube coupling hole. The inner end of the tube coupling hole is cylindrical and of about the same diameter as the tube to closely receive it; this minimizes the "dead" space around the end portion of the tube up to the seal, which may contain solvent that will mix with the sample. The most common tube size, which may be considered to be the "standard" tube size, is a tube of 1/16th inch outside diameter. Thus, most injector and column frames have tube-receiving holes whose inner ends are cylindrical and of a diameter of about 1/16th inch.

The size of the cavity between the extreme tip of the tube and a shoulder at the inner end of the tube coupling hole, varies in size, and can be substantial if the tip of the tube is not cut perfectly square at the end, if the loop is not pushed completely into the tube coupling hole, or if there is a burr or particle trapped between the tip of the tube and the inner end of the hole. The increased dispersion resulting from a larger cavity, is generally not important where a medium to larger sample is stored and is analyzed by a medium to larger column. However, in some situations, the sample volume is no more than about 2 uL (microliters) and is analyzed by a column of about 1 to 2 mm (millimeters) inside diameter. The dispersion caused by a larger than usual cavity at the end of a standard size tube can be significant. For example, a one-hundredth inch length between the tip of a standard size tube and the end of the tube receiving hole, can increase the dispersion by 22 uL$^2$ (microliters squared) if the sample is injected at a rate of 200 uL/min. It is very difficult to see, by the unaided eye, that the ferrule which holds the tube is put on with the tubing too short by only one-hundredth inch.

It is possible to minimize the "dispersion volume" at the end of a tube, by using a much smaller diameter tube when small volumes of a sample are to be analyzed. For example, a tube having an outside diameter of 0.020 inch can be used instead of a standard tube of 0.0625 inch, with the cross sectional area of the outside of the smaller tube being about one tenth that of the larger tube. The length of any gap at the end of the smaller tube is likely to be smaller than for the larger tube, but even for the same length of gap the volume of solvent trapped in the gap will only be about one tenth as much. Such a small diameter tube is difficult to use for larger fluid samples, since it may require very high pressures to rapidly pump out the sample from the tube and a much longer length of tube is required to hold the sample. An injector or column frame which was constructed to readily receive a standard size tube and also a much smaller diameter tube, and effective to seal to either one of them, with a minimum dispersion gap for the smaller size tube, all in a sample and low cost arrangement that enables easy switching between tube sizes, would be of considerable value.

SUMMARY OF THE INVENTION

In accordance with one embodiment of the present invention, a tube-connecting frame of a fluid analyzing system is provided, which can be readily coupled not only to a predetermined large size tube for usual operation with average to larger samples, but which can also couple to a smaller diameter tube of predetermined size for transference of small samples with minimum dispersion of the sample. The frame includes a tube coupling hole with an inner portion which is cylindrical and of a diameter substantially equal to the smaller tube diameter to closely receive it. The tube coupling hole also has a larger diameter middle hole portion which can closely surround the tip of the larger diameter tube, the middle hole portion including a tapered region, and the hole also having a threaded outer portion. Ferrules are provided, each with a tapered forward portion that can seal to the tapered hole region, and each with a ferrule hole which closely receives a tube of predetermined size. When the small diameter tube is to be used, it is inserted through a first ferrule which closely surrounds it; the end portion of the tube is pressed firmly into the inner end portion of the tube coupling hole of the frame, and the ferrule is sealed to the tapered hole portion. When the larger size tube is to be used, it is held in place and sealed by a second ferrule that closely receives the larger tube.

The larger sized tube can be held with its tip lying substantially against the tapered hole portion. Although this leaves a substantial gap between the tip of the larger sized tube and the extreme inner end of the tube coupling hole, the larger sized tube can be used with medium to larger sized samples where the resulting increased dispersion is not of great importance.

The novel features of the invention are set forth with particularity in the appended claims. The invention will be best understood from the following description when read in conjunction with the accompanying drawings.

BRIEF DESCRIPTION OF THE DRAWINGS

FIG. 1 is a sectional view of a portion of a sample injector constructed in accordance with the present invention, showing a smaller diameter tube in place.

FIG. 2 is a view similar to that of FIG. 1, but with a larger diameter tube in place.

DESCRIPTION OF THE PREFERRED EMBODIMENTS

Figure 3:
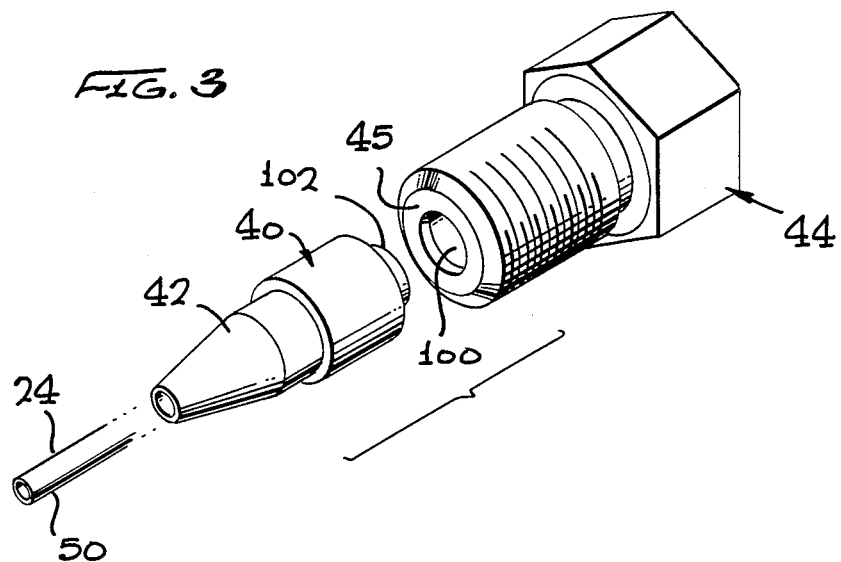
FIG. 3 is an exploded perspective view of part of the apparatus of FIG. 1.

FIG. 1 illustrates an apparatus 10 of a chromatographic analyzing system, which includes an injector 12 that can receive a fluid sample to be analyzed at a low pressure such as atmospheric pressure, and which can inject the sample into a chromatographic column for analysis. Systems of this type are well known, and an example of one of them is shown in U.S. Pat. No. 4,182,184. The injector includes a rotor 16 at which the fluid sample is injected, as from a hand-operated syringe inserted to the end of a rotor port 18, to flow the sample into a stator port 20 of a stator frame 22. The sample flows into a storage loop in the form of a tube 24. After the sample has been injected into the tube 24, the rotor 16 is turned to align the stator port 20 with another rotor port that leads to a chromatographic column. Also, an end of the tube opposite the end shown in FIG. 1, is coupled to a high pressure pump, which pumps a mobile phase, often referred to as a solvent, in the direction of arrow 26, to move the sample out of the tube 24 through the rotor and into the chromatorgraphic column for analysis.

The frame 22 of the injector includes a tube coupling hole 30 which couples to the tube 24 of the sample storage loop. The hole 30 includes an inner end portion 32 which is cylindrical and of a diameter substantially equal to the diameter A of the tube 24. The hole also includes a larger diameter middle hole portion 34 with a tapered hole region 36 which can be seen to occupy the entire length of the middle hole portion. The hole also includes a threaded outer portion hole portion 38. The tube is held and sealed to the tube coupling hole by a first ferrule 40. The ferrule 40 has a tapered forward outside surface 42 which can seal to the tapered hole region 36. A screw 44 which can threadably engage the outer hole portion 38, has an abutting portion 45 that presses against the ferrule to press its tapered forward surface against the tapered hole region to seal thereagainst.

The tube 24 can be installed by projecting it through a hole 46 in the ferrule that can closely surround the tube, with an end portion 50 of the tube projecting a considerable distance forward of the forward end of the ferrule. The tube with the ferrule 40 and screw 44 thereon is then moved fully into the hole until the tip 52 of the tube abuts a shoulder 54 formed at the inner end of the tube coupling hole. The screw 44 is then turned to advance it into the hole, while the tube continues to be pressed forwardly toward the bottom of the hole, until the screw presses the ferrule 40 tightly against the tapered hole portion to seal it thereagainst. The ferrule forms a tooth 56 which bites into the tube to prevent the tube from being "blown out" when high pressure is applied.

FIG. 2 illustrates the injector 12 and stator frame 22, when a larger size tube 60 of an outer diameter B is installed thereon. The outside diameter B of tube 60 is more than 50% greater than the outside diameter A of the smaller tube 24, and more than 50% greater than the diameter of the inner hole portion 32. The tube is held and sealed in place by a second ferrule 62 which has a tube-receiving hole 64 that closely surrounds the larger diameter tube 60. The ferrule also has a tapered forward outside surface 66 that can seal against the tapered hole region 36. The ferrule also forms a tooth 70 that bites into the tube to prevent its blowout. The tube has a forward tip 72 that is intended to substantially abut the tapered hole region 36 to minimize or substantially eliminate mixing of the sample with solvent that may have become trapped in the region 74 between the tube end and the sealed ferrule location. The larger tube 60 is installed by first installing the screw 44 and second ferrule 62 over the tube 60, and with the tip 72 of the tube projecting beyond the end of the ferrule. The tube is then pushed into the hole until its tip abuts the tapered surface, and the screw 44 is tightened to seal the ferrule to the tapered hole region.

The larger tube 60 is preferably a "standard" tube of 1/16th inch, or 0.0625 inch, outside diameter which is the most commonly used tube size in liquid chromatography. Applicant has used a smaller tube 24 of a diameter A of 0.020 inch (0.5 mm) outside diameter. The larger tube 60 is preferably used for holding the larger volume samples such as 50 uL and greater, which enable a sample loop formed of the tube 60 to be of moderate length and which enables the sample to be rapidly pumped out using moderate pressures. For such moderate to larger volume samples, the increase in dispersion caused by any mixing of the sample with the solvent trapped in the region 74 is generally not of considerable significance. The inner end portion 32 of the coupling hole has a diameter equal to or smaller than the inside diameter of the tube 60, so the hole portion 32 does not constitute a mixing cavity. Only the tapered region 113 and region 74 act as mixing cavities that increase dispersion. The increase in dispersion caused by regions 74, 113 is generally not of considerable significance, even if the tip 72 of the tube does not closely abut the tapered hole region. For smaller samples such as about 20 uL and less, the smaller diameter tube 24 is preferably used. Even if the tip 52 of the small diameter tube is spaced from the shoulder 54, the small diameter of the inner hole portion results in only a very small dead volume which can hold solvent that would mix with the sample. Also, any gap around the end portion 50 of the small diameter tube causes minimum dispersion because the volume of solvent that can lie in such a gap is small due to the very small diameter of the inner hole portion and tube. The fact that a technician can rapidly switch between the 0.625 inch diameter larger tube 60 and the 0.020 inch diameter smaller tube 24 facilitates use of the proper size tube for the particular sample volume to be analyzed.

Figure 4:
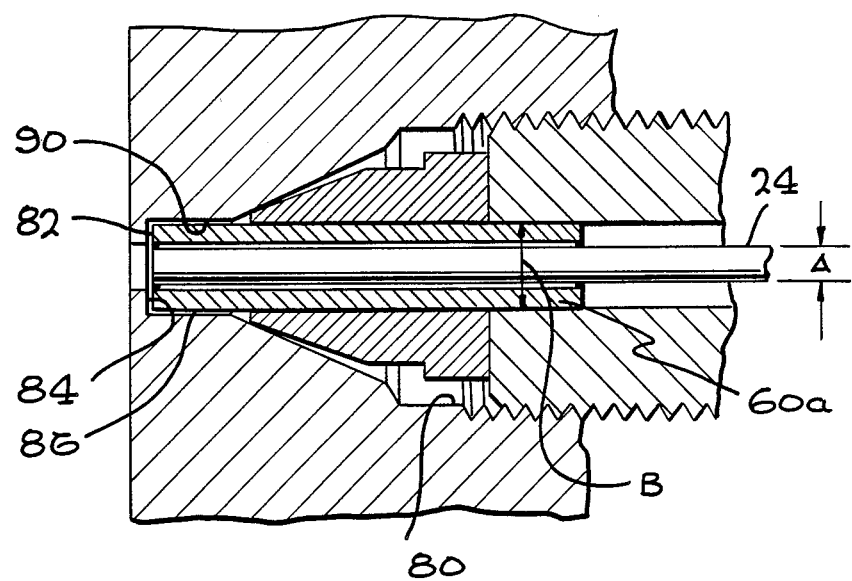
FIG. 4 is a partial sectional view of an alternate coupling system.

FIG. 4 shows a technique that has been used by applicant to enable a small diameter tube 24 of diameter A, to be used in a tube coupling hole 80 designed to receive a larger diameter tube of diameter B. This involves brazing a short length of the larger diameter tube 60 to the end of the smaller diameter tube 24. This had the disadvantage of the effort in brazing the larger diameter tube into place. Also, substantial dispersion was possible due to the large diameter of dead space in the region 82 between the tip of the brazed together tubes and a shoulder 84, due to the tubes not being cut perpendicular to their axes, or the presence of a burr at the end of the tube, or the presence of dirt at the end of the hole of the tube not being positioned to closely abut the inner end of the hole. Also, the gap 86 between the inner hole portion 90 and the outside of the larger tube has a much larger volume than for the smaller diameter tube 24.

Applicant has constructed and tested apparatus of the type shown in FIGS. 1-3, using ferrules 40, 62 and a screw 44 all of stainless steel, which is the material of the tubes. The same screw 44 was useful with each ferrule, which minimized the number of different parts that must be kept on hand. For the larger tube of FIG. 2, the tube 60 itself keeps the ferrule 62 and screw 44 aligned, because the screw 44 has a hole 100 that closely surrounds the larger diameter tube 60. For the first ferrule 40 of FIG. 1, the ferrule is provided with a rear portion 102 of about the same diameter as the tube 60 to closely fit into the screw hole 100, to align the screw and first ferrule. The ferrule 40 has a hole 46 that closely surrounds the first tube, but which extends only part of the length of the ferrule to reduce the length along which the precision hole must be formed. The gap 104 between the smaller diameter tube and the inner end portion 32 of the hole was about 1 to 2 thousandths inch. The taper of the tapered hole region 36 was 40 degrees.

It would be possible to form the tube coupling hole so its middle portion had a larger cylindrical hole part, shown at 110 in FIG. 2. Such a hole part could closely receive the larger diameter tube 60 and provide a shoulder at 112 perpendicular to the tube axis against which the larger tube can abut. However, this gives rise to the possibility that the smaller diameter tube will lie abutting the shoulder 112 instead of entering the hole inner end portion 32. Also, if the larger tube is used only for medium to larger samples, the reduction in dispersion provided by hole part 110 would not be important.

Thus, the invention provides an apparatus for use with a chromatographic analyzing system, and especially an injector, which facilitates switching between larger and smaller sized tubes, which minimizes dispersion when the smaller sized tube is used (when smaller samples are used wherein dispersion must be minimized) and which also maintains dispersion at a fairly low level for the larger sized tube. A frame which has a tube coupling hole in which the tubes are received, has a cylindrical inner hole portion of a diameter to closely receive and surround an end of the small tube, a larger diameter middle hole portion which includes a tapered region that can closely receive and surround the end of a larger size tube, and a threaded outer hole portion. Two ferrules are used, which each seal to the tapered hole portion, one having a hole that closely surrounds the smaller tube and the other having a hole that closely receives the larger tube.

Although particular embodiments of the invention have been described and illustrated herein, it is recognized that modification and variations may readily occur to those skilled in the art, and consequently, it is intended that the claims be interpreted to cover such modifications and equivalents.

What is claimed is:

1. Apparatus for use with a liquid chromatographic analyzing system for coupling not only to a tube of standard-size 1/16th inch outside diameter for usual operation with average to large samples but also to a smaller diameter tube of predetermined smaller outside diameter for operation with small samples with minimum dispersion of the sample, where the outside diameter of the standard-size tube is at least 50% greater than the outside diameter of the smaller diameter tube, comprising:

a frame having a tube coupling hole with an inner end portion which is cylindrical and of a diameter substantially equal to said smaller tube diameter to closely receive and surround an end of said smaller tube, said coupling hole having a larger diameter middle hole portion which can receive and closely surround the end of said standard-size tube with said middle hole portion including a tapered hole region, and said coupling hole having a threaded outer hole portion:
   first and second ferrules, each having a tapered forward outside surface which can seal to said tapered hole region, and an inside surface with a cylindrical shape inside that closely receives a different one of said tubes; and
   a screw that has an outer portion that can threadably couple to said threaded outer hole portion and an abutting portion that can abut one of said ferrules to press it forwardly.

2. The apparatus described in claim 1 wherein:
said standard-size tube has an outside diameter that is at least twice the diameter of said inner end portion of said coupling hole.

3. The apparatus described in claim 1 wherein:
said screw has a hole which is of a size to closely surround said standard-size tube;
said first ferrule has a hole which closely surrounds said smaller diameter tube, and has a rear portion of about the same outside diameter as said standard-size tube to closely fit into said screw hole, whereby to align said screw and first ferrule.

4. The apparatus described in claim 1 including:
a tube of said standard size extending through said second ferrule and screw and having an extreme tip lying substantially against said tapered middle hole region at a location spaced from said inner end portion of said hole, said screw being threaded into said outer hole portion and said second ferrule being compressed against said tapered hole region.

5. The apparatus described in claim 1 including:
a small diameter tube of said smaller outside diameter extending through said first ferrule and screw and having a forward tube end lying in said inner end portion of said tube coupling hole, said screw being threaded into said outer hole portion and said first ferrule being compressed against said tapered hole region.

6. In a sample injection apparatus which can receive a sample at low pressure and then inject it at high pressure into a chromatographic column device for analysis, the improvement comprising:
   an injection apparatus frame having a tube coupling hole with a cylindrical inner hole portion of a first small diameter, a tapered middle hole portion, and a threaded outer hole portion;
   a first ferrule which has a hold of a diameter to closely receive a tube of said first small diameter, and a tapered forward portion for sealing to said tapered middle hole portion;
   a second ferrule which has a larger hole of a diameter to closely receive a tube of a second diameter that is at least about twice said first diameter, and a tapered forward portion for sealing to said tapered middle hole portion;
   a screw which is threadable in said outer hole portion and which can press the forward portion of at least one of said ferrules against said tapered middle hole portion, said screw having a hole which can receive a tube of at least said first diameter;
   a first tube with an end portion being of substantially said first diameter, which can lie in a first position in extension through said first ferrule and with an end portion lying in said inner hole portion;
   a second tube with a tip, and being of said second diameter, which can lie in a second position in extension through said second ferrule and with said tip lying substantially against said tapered middle hole portion, when said first tube and first ferrule are not in said hole.

7. The improvement described in claim 6 wherein:

said second tube has a diameter of about 1/16th inch and said first tube has a diameter of about 20 thousandths inch.

8. A method for enabling the installation of a second tube of a larger diameter and then a first tube of a smaller diameter in a frame of a chromatographic analyzing system comprising:

forming a tube coupling hole in said frame, with a cylindrical inner hole portion of substantially said first diameter, a tapered middle hole portion, and an outer hole portion;

projecting the end portion of a second tube of said second diameter through a second ferrule, pressing the tip of said second tube against said tapered hole portion at a location spaced outwardly from said inner hole portion, and pressing a tapered forward portion of said second ferrule against said tapered hole portion to seal said second ferrule to said coupling hole and to said second tube;

removing said second tube and second ferrule from said hole;

projecting the end portion of a first tube of said first diameter through a first ferrule, pressing the end portion of said first tube deeply into said inner hole portion and pressing said first ferrule against said tapered hole portion to seal said first ferrule to said coupling hole and to first tube.

* * * * *